(12) United States Patent
Kim et al.

(10) Patent No.: US 8,349,335 B2
(45) Date of Patent: Jan. 8, 2013

(54) METHODS FOR PREPARING CHLOROPHYLL A AND CHLORIN E6

(75) Inventors: Yong Chul Kim, Gwangju (KR); Zee Yong Park, Gwangju (KR); Hyo Jun Kim, Busan (KR)

(73) Assignee: Gwangju Institute of Science and Technology, Gwangju (KR)

( * ) Notice: Subject to any disclaimer, the term of this patent is extended or adjusted under 35 U.S.C. 154(b) by 446 days.

(21) Appl. No.: 12/513,225

(22) PCT Filed: May 3, 2007

(86) PCT No.: PCT/KR2007/002177
§ 371 (c)(1),
(2), (4) Date: May 1, 2009

(87) PCT Pub. No.: WO2008/054050
PCT Pub. Date: May 8, 2008

(65) Prior Publication Data
US 2010/0113766 A1    May 6, 2010

(30) Foreign Application Priority Data
Nov. 3, 2006    (KR) .................. 10-2006-0108058

(51) Int. Cl.
*A01N 65/00*    (2009.01)
*A61K 36/02*    (2006.01)
*C12N 1/12*    (2006.01)
*C07B 47/00*    (2006.01)
*C07D 487/22*    (2006.01)

(52) U.S. Cl. ................. 424/195.17; 435/257.3; 540/145
(58) Field of Classification Search .................. None
See application file for complete search history.

(56) References Cited

OTHER PUBLICATIONS

Sartory, D.P. and Grobbelaar, J.U. (1984) Extraction of chlorophyll a from freshwater phytoplankton for spectrophotometric analysis. Hydrobiologia 114, 177-187.*
Website Document Entitled: "Easy Science Project: Chlorophyll Extraction." (available at www.scienceprojectlab.com/easy-science-project-chlorophyll.html). Dowloaded from website Aug. 29, 2011.*
Iriyama et al. (1974) J. Biochem. vol. 76 Issue 4 pp. 901-904.*
Wun et al., "A Solvent Partitioning Procedure for the Separation of Chlorophylls from Their Degradation Products and Carotenoid Pigments," Hydrobiologia 71:289-293, 1980.
International Search Report from International Application No. PCT/KR2007/002177, dated Aug. 17, 2007.

* cited by examiner

*Primary Examiner* — Chris R Tate
*Assistant Examiner* — Russell Fiebig
(74) *Attorney, Agent, or Firm* — Clark & Elbing LLP

(57) ABSTRACT

The present invention relates to a method for preparing chlorophyll-a and chlorin e6. This invention extracts chlorophyll-a by use of undisrupted *chlorella* cells themselves, thereby preparing chlorin e6 from the chlorophyll-a extract. The high contents of chlorophyll-a may be obtained by the pretreatment procedure of *chlorella* cells themselves selected in this invention. The present method is performed according to relatively simple procedures, and is suitable in the mass production of chlorin e6.

4 Claims, 18 Drawing Sheets

METHODS FOR PREPARING CHLOROPHYLL A AND CHLORIN E6

CROSS-REFERENCE TO RELATED APPLICATIONS

This application claims priority under 35 U.S.C. §371 from international application PCT/KR2007/002177, filed May 3, 2007, which claims priority from Korean Patent Application 10-2006-0108058, filed Nov. 3, 2006.

FIELD OF THE INVENTION

The present invention relates to a method for preparing chlorophyll-a and chlorin e6.

DESCRIPTION OF THE RELATED ART

Chlorin e6 is a photosensitive material used in photodynamic therapy of cancer.

U.S. Pat. No. 5,330,741 discloses the method for preparing chlorin e6. According to the method of U.S. Pat. No. 5,330,741, biomass is treated with acetone 2-3 times in order to extract chlorophyll-a, the biomass is filtrated or centrifuged, the extract is evaporated, treated with acid in order to remove magnesium ion from the chlorophyll molecule and to hydrolyze the phytyl ester group. Methyl alcohol being added for concurrent esterification, the reaction mass is treated with water, pheophorbide α derivative is extracted with chlorous methylene, the extract is neutralized, washed with water, evaporated, chromatographed on aluminium oxide. Methylpheophorbide α is crystallized out of the mixture of chlorous methylene-methanol and the resulting pheophorbide α derivative is reacted with a strong inorganic base in the presence of oxygen in pyridine-diethyl ether-n-propanol. The reaction mass is then treated with water. The water phase is acidified until it reaches pH 4. Unstable chlorin is extracted with chlorous methylene, the extract is evaporated, and unstable chlorine is redissolved in tetrahydrofurane. The resulting solution is then evaporated. This procedure is repeated until absorption at 700 nm ceases to increase. The resulting purpurin 18 is dissolved in tetrahydrofurane, esterified with diazomethane, and mixed with lysine water solution in chlorous methylene in the presence of pyridine. The mixture is stirred for 12 hr at room temperature. The solvents are removed in high vacuum and the resulting crude product is purified by reverse phase high-performance liquid chromatography (HPLC). The solvents are removed by lyophilisation. The PS is dissolved in phosphate buffer in order to obtain an injection solution for PDT, 0.1N NaOH solution is added, the pH is adjusted to a physiological value of pH 7.35 with 0.1N HCl and the solution is filtrated through a microporous filter.

However, the disadvantages of this method are: low reproducibility, laboriousness (the use of high vacuum, crystallization, column chromatography and HPLC, and long duration of the reaction with lysine), the use of high toxic and inflammable reagents (diazomethane, pyridine, methanol, tetrahydrofurane, diethyl ether). These disadvantages make the method unsuitable for the pharmaceutical and food industry.

According to Korean Pat. Appln. Publication No. 2004-0025911, Spirulina biomass is treated with acetone until chlorophyll-a is completely extracted. The biomass is filtered out or centrifuged, the extract is treated with acid in order to remove magnesium ion from the chlorophyll molecule, the extract is neutralized and precipitated pheophytin a is filtered out. Then pheophytin a is hydrolyzed in the mixture of hydrochloric acid-acetone-hexane. Six to sixteen ml acetone, 0.6-6-ml hexane and 5-10 ml concentrated hydrochloric acid is used for every 1 g of crude pheophytin a. The mixture is heated up to 40-60° C. and stirred for 20 min-1 hr. Hexane (6-16 ml) is then added and the organic phase is washed with the mixture of acetone and hydrochloric acid (2-10:1), while the water phase is washed with hexane. Precipitated pheophorbid a is filtered out, washed with water, recrystallized out of the acetone-water mixture, and air dried until its weight becomes constant. Then pheophorbid a is dissolved in acetone. A strong inorganic base is added in the form of water solution of 0.05-1.00% concentration with stirring for 5-30 min at 30-60° C. An extra volume of strong inorganic base is further added in the form of water solution of 1-50% concentration, the mixture is heated for 20-90 min at 40-60° C., and neutralized with diluted hydrochloric acid. Chlorin e6 precipitate is separated by centrifugation, washed with distilled water until the acid reaction disappears, and 55-80% of chlorin e6 is obtained.

This method also has disadvantages such as the complexity of the procedure and the use of reagents unsuitable in the food and pharmaceutical field.

Throughout this application, several patents and publications are referenced and citations are provided in parentheses. The disclosure of these patents and publications is incorporated into this application in order to more fully describe this invention and the state of the art to which this invention pertains.

DETAILED DESCRIPTION OF THIS INVENTION

The present inventors have made intensive researches to develop a method of preparing chlorin e6 with higher yield in a relatively simple and mass production manner from *chlorella* belonging to green algae. As a result, the inventors have found the effective protocols for preparing chlorin e6 with unique pre-treatment procedures of *chlorella*.

Accordingly, it is an object of this invention to provide a method for preparing chlorophyll-a.

It is another object of this invention to provide a method for preparing chlorin e6.

Other objects and advantages of the present invention will become apparent from the detailed description to follow taken in conjugation with the appended claims and drawings.

In one aspect of the present invention, there is provided a method for preparing chlorophyll-a comprising the step of treating an undisrupted intact *chlorella* with an organic solvent.

To effectively prepare chlorin e6, the present inventors have selected *chlorella* as a suitable starting material for this purpose.

According to conventional methods known to one of skill in the art, *chlorella* cells first are lysed and the extraction of chlorophyll-a is carried out using the cell lysates. However, departing from the conventional processes and approaches, the present inventors have succeeded in preparing chlorin e6 with much higher yield by use of undisrupted intact *chlorella* cells. Considering the conventional methods, the results of the present method leading to the successful extraction of chlorophyll-a are very surprising and unexpected.

The term "intact *chlorella*" as used herein, refers to undisrupted *chlorella*, having the same meaning as "live *chlorella*" used in general to one skilled in the art. Where the extraction and isolation of intracellular materials are generally carried out, the cell disruption procedures (e.g., ultrasonication) are inevitably accompanied. However, undisrupted *chlorella* cells themselves are used in the present invention.

The present invention using undisrupted *chlorella* cells has plausible advantages: excellent extraction efficiency of chlorophyll-a and avoidance of chlorophyll-a oxidation induced in cell disruption procedures.

Organic solvents that may be used in the present method include various organic solvents known to one skilled in the art, e.g. (i) absolute or hydrous lower alcohol containing 1-4 carbon atoms (methanol, ethanol, propanol, butanol, etc.), (ii) a mixture of lower alcohol and water, (iii) acetone, (iv) ethyl acetate, (v) chloroform, (vi) butyl acetate, (vii) 1,3-butyleneglycol, (viii) nucleic acid and (ix) diethyl ether may be used. Preferably, the organic solvent used in this invention is methanol or ethanol, more preferably ethanol.

*Chlorella* used in this invention may be any conventional *chlorella*, and preferably is seawater *chlorella*. More preferably, chlorella used in this invention is *Chlorella ellipsoidea, chiorella minutissima, Chlorella vulgaris, Chlorella fusca, Chlorella zofingiensis, Chlorella stigmataphora, Chlorella vulgaris* or *Chlorella pyrenoidosa*, and most preferably is *Chlorella ellipsoidea*.

In another aspect of the present invention, there is provided a method for preparing chlorophyll-a comprising the steps of: (a) treating *chlorella* with 30-80% ethanol to remove ingredients other than chlorophyll-a from the *chlorella*; and (b) treating the *chlorella* with 90-100% ethanol to extract chlorophyll-a, thereby obtaining a chlorophyll-a extract.

In still another aspect of the present invention, there is provided a method for preparing chlorophyll-a comprising the steps of: (a) treating *chlorella* with 80-100% ethanol to extract chlorophyll-a; and (b) treating the extract with dioxane to induce the precipitation of the chlorophyll-a.

The present inventors have made intensive studies to develop an effective method for preparing chlorophyll-a from *chlorella* as a precursor of chlorin e6. As a result, the inventors have found two protocols capable of preparing chlorophyll-a with high yield and purity.

Chlorophyll-a—Protocol A

Chlorophyll-a—Protocol A comprises the procedures of removing ingredients other than chlorophyll-a from the *chlorella* using a relatively lower concentration of ethanol, and extracting chlorophyll-a by use of a relatively higher concentration of ethanol.

According to a preferred embodiment, *chlorella* used in the present invention is undisrupted *chlorella* cells. In this invention, it is preferable to use *chlorella* cells themselves, as cells undisrupted by sonication. It is general to extract chlorophyll-a by treating a cell lysate with the organic solvent. However, according to a preferred embodiment, undisrupted *chlorella* cells themselves are used. The present invention using undisrupted *chlorella* cells has plausible advantages: excellent extraction efficiency of chlorophyll-a and avoidance of chlorophyll-a oxidation induced in cell disruption procedures.

According to a preferred embodiment, *chlorella* used in the present invention is seawater *chlorella*, more preferably, *Chlorella ellipsoidea, Chlorella minutissima, Chlorella vulgaris, Chlorella fusca, Chlorella zofingiensis, Chlorella stigmataphora, Chlorella vulgaris* or *Chlorella pyrenoidosa*, and most preferably, *Chlorella ellipsoidea*.

One of the striking features of this invention is the performance of pretreatment procedures that eliminate ingredients other than chlorophyll-a from *chlorella* prior to extracting chlorophyll-a from *chlorella*. These pretreatments enable chlorophyll-a to be extracted with high purity (contents percentage).

The procedure to eliminate other ingredients is performed by treating *chlorella* with 30-80% ethanol. The reasons for the utilization of ethanol are: (i) ethanol shows the highest efficiency in the elimination of other ingredients, and (ii) ethanol is harmless to humans and is preferred where the final product chlorin e6 is used as raw materials for food. The concentration of ethanol used in such procedures is 30-80%. Where ethanol is used in a concentration of less than 30%, the elimination efficiency of other ingredients becomes much lower. Where ethanol is used in a concentration of more than 80%, the extraction efficiency of chlorophyll-a sharply drops due to the elimination of chlorophyll-a as well as other ingredients.

Preferably, the concentration of ethanol in the step (a) is 30-68%, more preferably, 50-65%, still more preferably, 58-62%, most preferably, about 60%.

The step (a) is performed at least once, preferably 2-7 times, more preferably 3-6 times, most preferably 5-6 times. Where the step (a) is repeatedly performed, other ingredients in *chlorella* are eliminated by suspending *chlorella* cells in ethanol and centrifuging for precipitation.

To *chlorella* cells pretreated to eliminate other ingredients, 90-100% ethanol is added to extract chlorophyll-a. At this time, the ethanol concentration of less than 90% greatly decreases the extraction efficiency.

Preferably, the concentration of ethanol in the step (b) is 95-100%, more preferably, 98-100%, most preferably, about 100%.

The yield of chlorophyll-a by the method of protocol A is 5-15%, preferably 6-12%, more preferably 7-9%. The yield is calculated as a percentage of the weight of obtained chlorophyll-a to the dried weight 1 g of *chlorella* used.

The purity of chlorophyll-a by the method of protocol A ranges from 70 to 90%, preferably 70-85%, more preferably 72-80%.

Chlorophyll-a—Protocol B

Chlorophyll-a—Protocol B is a simple procedure for obtaining chlorophyll-a with high yield that uses a high concentration of ethanol and dioxane, since the procedure in protocol A for eliminating other ingredients is omitted.

Details for *chlorella* used in chlorophyll-a—protocol B are the same as protocol A described above.

First step of chlorophyll-a—protocol B is the step of extracting chlorophyll-a from *chlorella* using a concentration of 80-100% ethanol. At this time, the use of an ethanol concentration of less than 80% greatly decreases the extraction efficiency.

Preferably, the concentration of ethanol in the step (a) is 90-100%, more preferably, 98-100%, most preferably, about 100%.

The second step of chlorophyll-a—protocol B is the step of precipitating chlorophyll-a using dioxane. Through this step, chlorophyll-a with a high purity as well as solid phase by precipitation may be obtained. The amounts of dioxane used per 1 L of the chlorophyll-a extract are preferably but not limited to 50-250 ml, more preferably 100-200 ml, and most preferably 120-160 ml. In this case, the amount of dioxane used is 100%.

According to a preferred embodiment, the step is carried out by adding water to the extract after the addition of dioxane. The amounts of water to 1 L of chlorophyll-a extracts are preferably but not limited to 50-250 ml, more preferably 100-200 ml, and most preferably 120-160 ml.

According to a preferred embodiment, the method further comprises the step of cooling the resultant of the step (b) at less than −10° C. after the step (b) to induce better precipitation of chlorophyll-a. More preferably, the temperature ranges from −15° C. to −30° C., and most preferably −18° C. to −25° C.

The yield of chlorophyll-a by the method of protocol B is 3-15%, preferably 4-10%, and more preferably 4-6%. The purity of chlorophyll-a is 70-98%, preferably 75-95%, and more preferably 80-90%.

In another aspect of the present invention, there is provided a method for preparing chlorin e6 comprising the steps of: (a)

treating the chlorophyll-a obtained by the method described above with an acid to eliminate $Mg^{2+}$ from chlorophyll-a, thereby obtaining pheophytin a; and (b) treating the pheophytin a with a base to obtain chlorin e6.

According to chlorin e6-protocol A, the method treats chlorophyll-a with an acid to eliminate $Mg^{2+}$ from chlorophyll-a, thereby obtaining pheophytin a. Chlorophyll-a and pheophytin a represented by the following formulas 1 and 2.

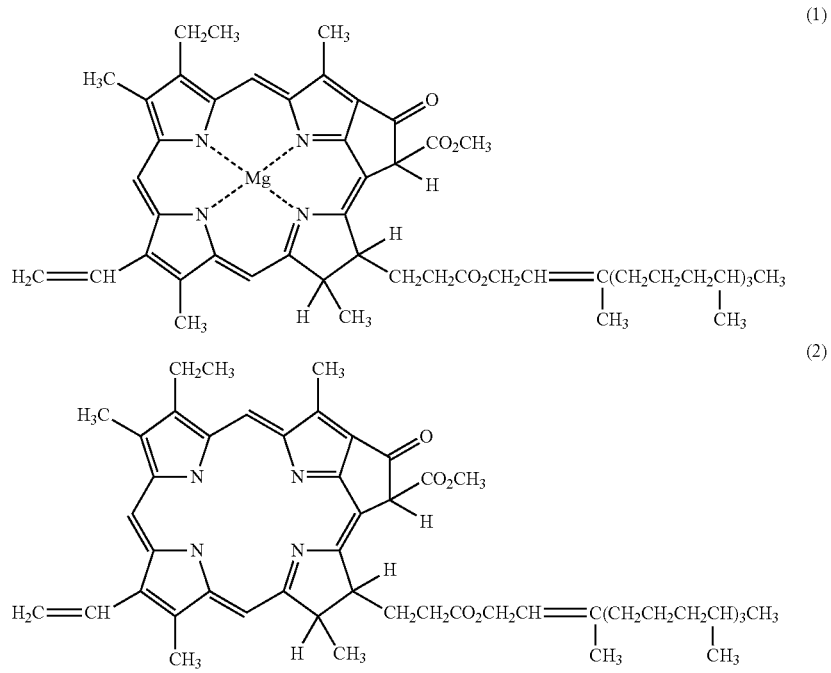

The present inventors have made intensive researches to develop a method of preparing chlorin e6 with higher yield in a relatively simple and mass production manner from *chlorella* belonging to green algae. As a result, the inventors have found effective protocols for preparing chlorin e6.

The method for preparing chlorin e6 of this invention is by use of chlorophyll-a obtained by the described two methods for preparing chlorophyll-a.

More specifically, where using chlorophyll-a prepared by chlorophyll-a—protocol A as a starting material, the present invention comprises the steps of: (a) treating *chlorella* with 30-68% ethanol to remove ingredients other than chlorophyll-a from the *chlorella*; (b) treating *chlorella* with 80-100% ethanol to extract chlorophyll-a, thereby obtaining a chlorophyll-a extract; (c) treating the chlorophyll-a with an acid to eliminate $Mg^{2+}$ from chlorophyll-a, thereby obtaining pheophytin a; and (d) treating the pheophytin a with a base to obtain chlorin e6.

More specifically, where using chlorophyll-a prepared by chlorophyll-a—protocol B as a starting material, the present invention comprises the steps of: (a) treating *chlorella* with 80-100% ethanol to extract chlorophyll-a; (b) adding dioxane to the extract to induce the precipitation of chlorophyll-a; (c) treating chlorophyll-a with an acid to eliminate $Mg^{2+}$ from chlorophyll-a, thereby obtaining pheophytin a; and (d) treating pheophytin a with a base to obtain chlorin e6.

Meanwhile, the present method for preparing chlorin e6 comprising the step for preparing pheophytin a using the acids and the step for preparing chlorin e6 using the bases, more specifically could be classified into two representative protocols.

Chlorin e6—Protocol A

Chlorin e6—Protocol A is performed in the presence of an ethanol solvent to prepare chlorin e6 from pheophytin a.

Where treating chlorophyll-a with the acid, $Mg^{2+}$ is eliminated from the formula 1, leading to the production of pheophytin a. Preferably the step (a) is performed by treating the chlorophyll-a extract with the acid to adjust pH of the chlorophyll-a extract to 1-5. At this time, a pH of more than pH 5 greatly decreases the extraction efficiency of $Mg^{2+}$. More preferably, pH of reactants in the step (a) is 1-3, most preferably 2-3.

The acids used in the step (a) may be various acids well-known to one skilled in the art, preferably the acid is inorganic acid, more preferably sulfuric acid and hydrochloric acid, and most preferably hydrochloric acid.

Chlorin e6 represented by the following formula 3 is finally obtained by treating the pheophytin a prepared by the procedure described above with the base.

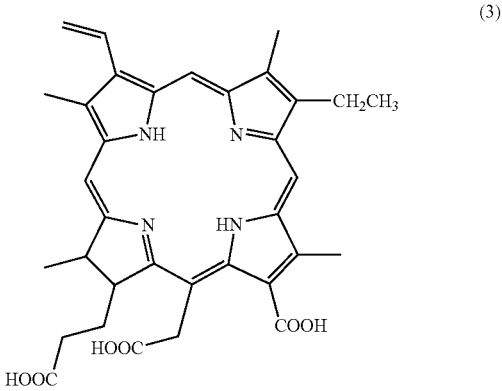 [SMILES: C=Cc1c(C)c2cc3nc(c(CC(=O)O)c4[nH]c(cc5nc(cc1[nH]2)C(C)=C5CC)c(C)c4C(=O)O)C(CCC(=O)O)C3C]

According to a preferred embodiment, the step (b) is performed by treating the pheophytin a with the basic solution, thereby being adjusted to pH 11-16, more preferably pH 13-14. The bases used in the step (b), may be various bases well-known to one skilled in the art, preferably the base is an inorganic base, and most preferably NaOH.

According to a preferred embodiment, the step (b) obtaining chlorin e6 is performed in the presence of the ethanol solvent.

According to a preferred embodiment, the precipitation of pheophytin a is induced by keeping in cold storage.

Pheophytin a is commonly obtained in the form of precipitates. Where preparing chlorin e6 by use of the ethanol solvent, the precipitate of pheophytin a is not directly dissolved in the ethanol solvent. Therefore, it is preferable to dissolve the pheophytin a precipitate with acetone prior to dissolving the pheophytin a precipitate in the ethanol solvent. Afterwards, acetone is eliminated (e.g., by evaporation) from acetone dissolving resultant and ethanol is added to pheophytin a for dissolving pheophytin a, followed by reacting the dissolved pheophytin a with a base to obtain chlorin e6.

According to a preferred embodiment, the chlorin e6-protocol A comprises the steps of (a) treating chlorophyll-a obtained by the above method with the acid to eliminate $Mg^{2+}$ from chlorophyll-a, thereby obtaining the precipitate of pheophytin a; (b-1) adding the acetone solvent to the precipitate of pheophytin a to obtain a solution of pheophytin a, followed by elimination of the acetone solvent; (b-2) adding ethanol to the residual pheophytin a to obtain the pheophytin a solution; and (b-3) treating the pheophytin a solution with the base to obtain chlorin e6.

According to a preferred embodiment, the method further comprises the step of neutralizing the resultant of the step (b) after the step (b). At this time, the resultant may be neutralized by various bases (e.g., HCl).

After the production of chlorin e6, chlorin e6 may be treated with a salt to produce a suitable salt form. For example, —COOH group of chlorin e6 is bound with sodium or ammonium by treating chlorin e6 with $NaHCO_3$ or $NH_4CO_3$, thereby obtaining chlorin e6 salt.

The purity of chlorin e6 by the chlorin e6-protocol A is 80-99%, preferably 85-99%, and more preferably 93-98%. Where using chlorella as a starting material, the yield of chlorin e6 ranges from 3 to 10%, preferably 3-8%, and more preferably 4-6%. The yield is calculated as a percentage of obtained chlorin e6 weights to the dried weight 1 g of used chlorella.

Chlorin e6—Protocol B

Chlorin e6—Protocol B is performed in the presence of an acetone solvent to prepare chlorin e6 from pheophytin a.

Details for step (a) in the chlorin e6-protocol B are the same as in the chlorin e6-protocol A described above. In addition, step (b) in the chlorin e6-protocol B is the same as in the chlorin e6-protocol A except for treating pheophytin a with a base in the presence of the acetone solvent.

According to the chlorin e6-protocol B, the pheophytin a precipitate formed in step (a) is dissolved in the acetone solvent, and the pheophytin a solution is directly treated with a base, thereby preparing chlorin e6.

According to a preferred embodiment, the chlorin e6-protocol B comprises the steps of: (a) treating chlorophyll-a obtained by the above method with the acid to eliminate $Mg^{2+}$ from chlorophyll-a, thereby obtaining the precipitate of pheophytin a; (b-1) adding the acetone solvent to the precipitate of pheophytin a to obtain a solution of pheophytin a; and (b-2) treating the pheophytin a solution with the base to obtain chlorin e6.

According to chlorin e6-protocol B, where using NaOH as a base, the chlorin e6 prepared has a final sodium salt form. According to the chlorin e6-protocol A, a separate treatment has to be conducted for obtaining chlorin e6 salt, but the protocol B may omit this procedure Chlorin e6—Protocol B is a more effective method for preparing chlorin e6 via a simple procedure relative to protocol A. In addition, despite chlorin e6-protocol B being a more simple procedure than protocol A, the purity of chlorin e6 finally prepared is much higher than for protocol A.

The purity of chlorin e6 by chlorin e6-protocol B is 90-99.99%, preferably 92-99.95%, more preferably 95-99.90%, and most preferably 99.0-99.90%. Where using chlorella as a starting material, the yield of chlorin e6 is 2-8%, preferably 3-8%, and more preferably 3-5%.

The summary of features and advantages of this invention is as follows:

(i) This invention extracts chlorophyll-a by use of undisrupted chlorella cells themselves, thereby preparing chlorin e6 from the chlorophyll-a extract.

(ii) The high contents of chlorophyll-a may be obtained by the pretreatment procedure of chlorella cells themselves selected in this invention.

(iii) The present method is performed according to relatively simple procedures, and is suitable in the mass production of chlorin e6.

BRIEF DESCRIPTION OF THE DRAWINGS

FIGS. 1a-1c show results extracting for 30 min, 90 min and 3 hr, respectively. An arrow presents the pick of chlorophyll-a.

FIGS. 1d-1f show results extracting for 30 min, 90 min and 3 hr, respectively. The arrow presents the pick of chlorophyll-a.

FIGS. 2b-2g show results analyzing at 1-6 times in a repeated washing procedure using 60% ethanol. The HPLC analysis shows the results for supernatants formed by washing.

FIG. 3a shows the HPLC chromatogram for pheophytin a formed according to the present method. The arrow presents the pick of pheophytin a.

Figure 1A:
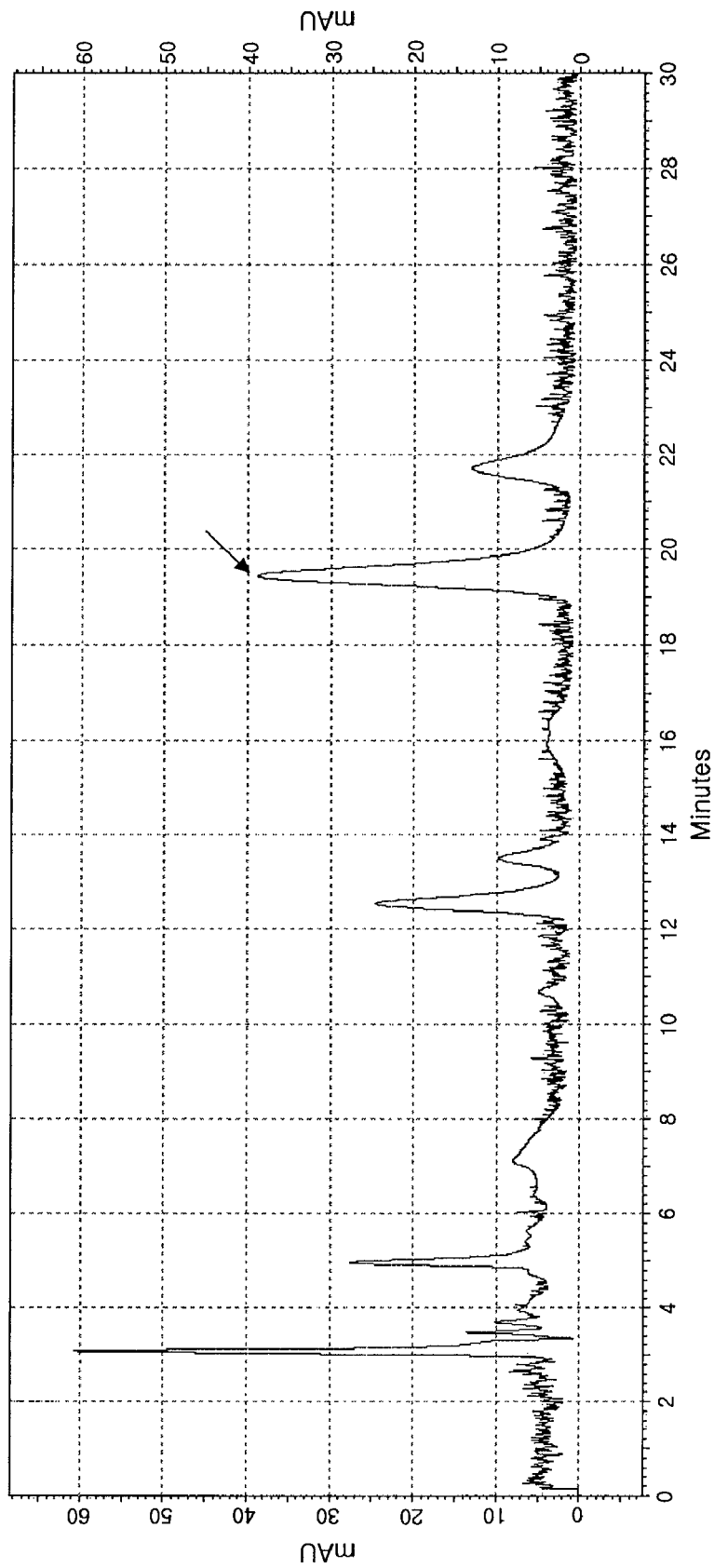
FIGS. 1a-1c are a HPLC (high pressure liquid chromatography) chromatogram showing ethanol extraction results for chlorophyll-a by use of disrupted chlorella.
Figure 1B:
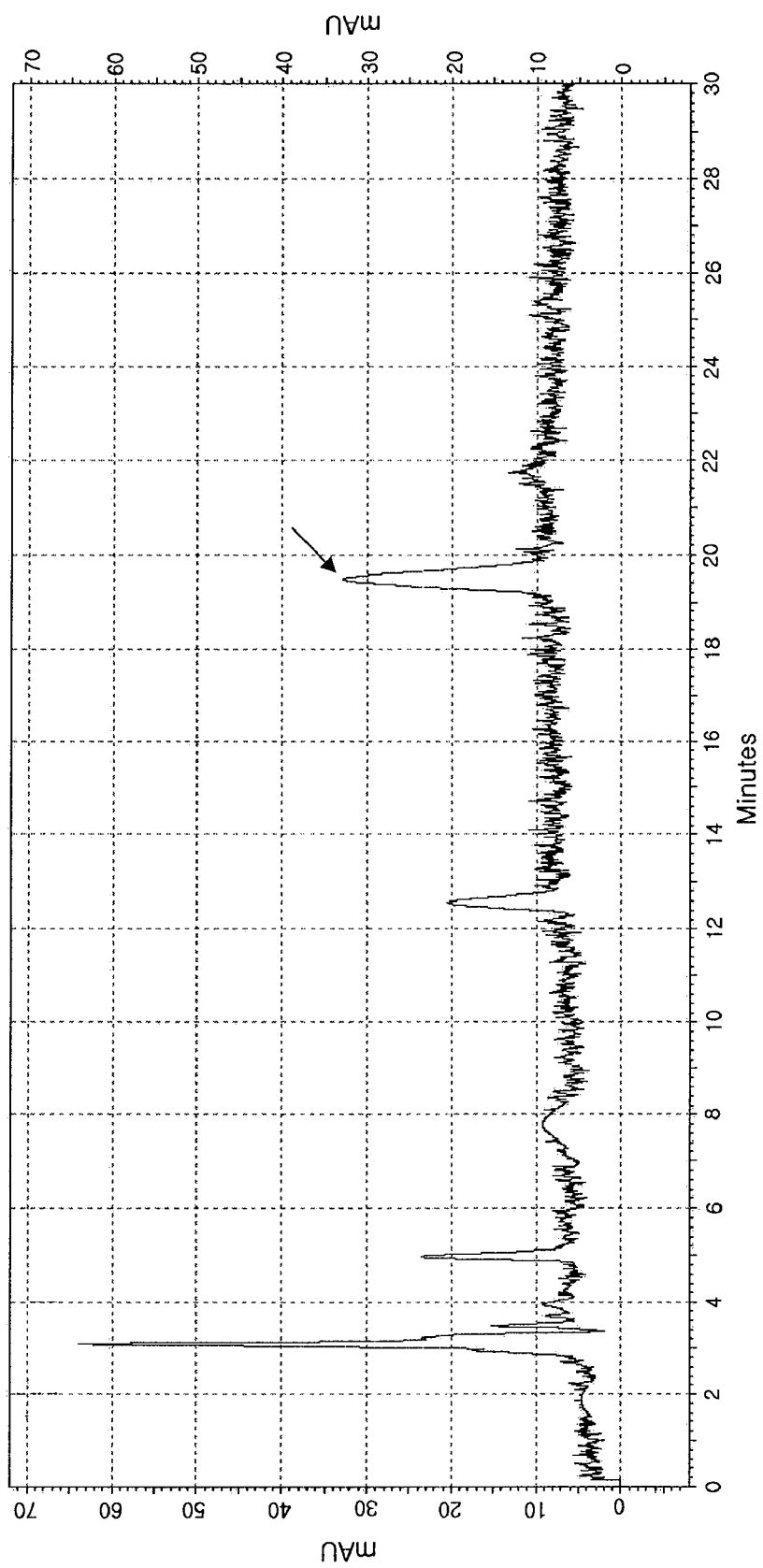
Figure 1C:
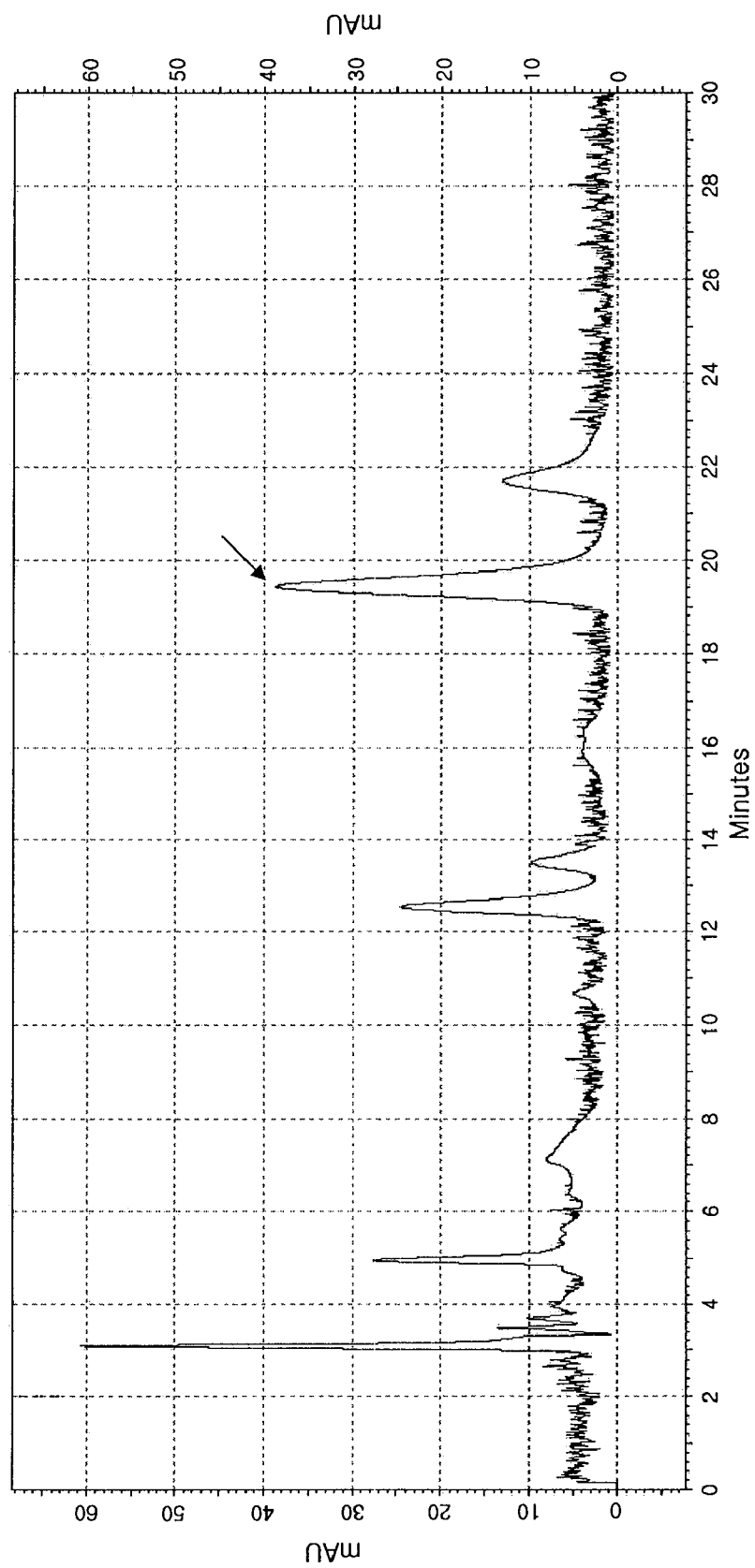
Figure 1D:
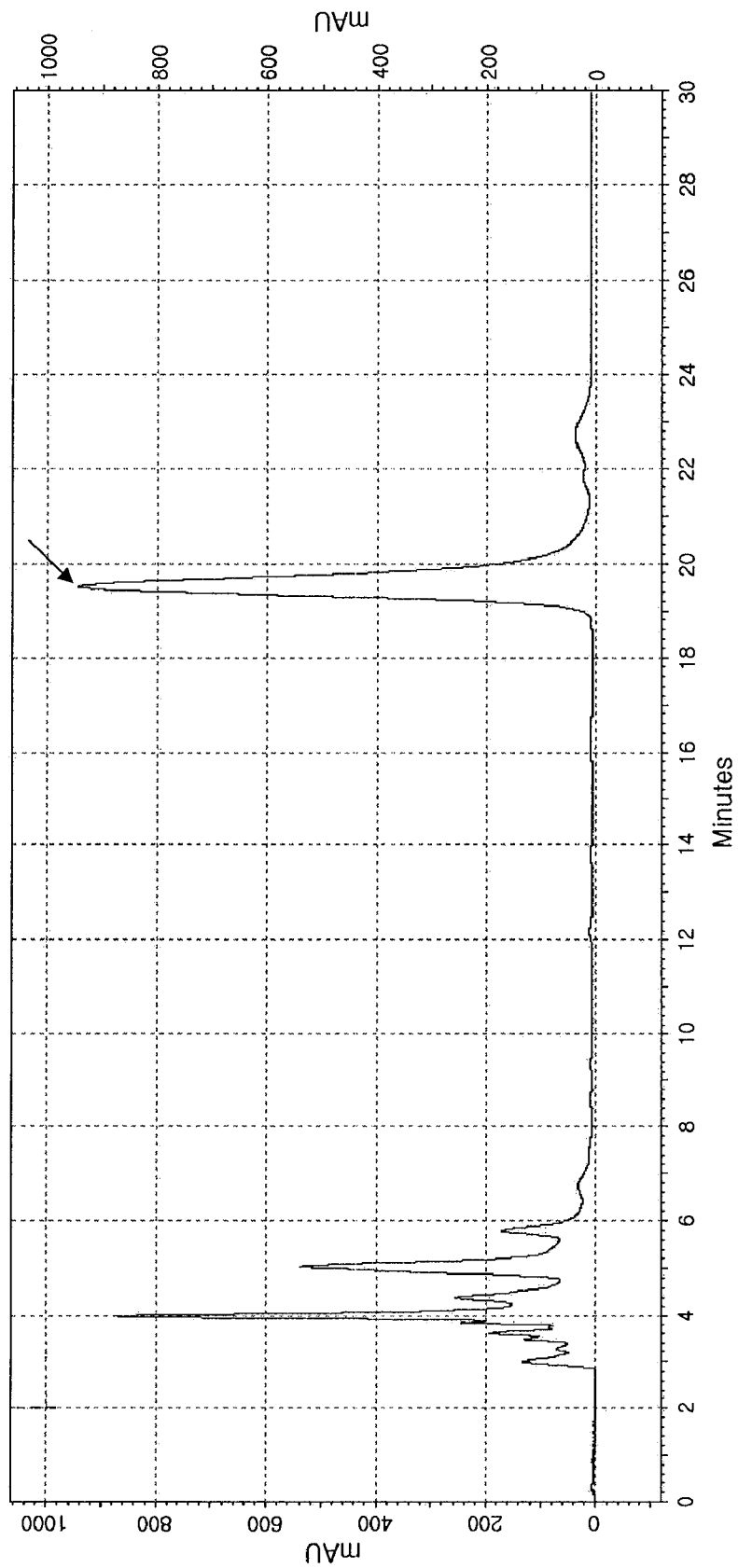
FIGS. 1d-1f are the HPLC chromatogram showing ethanol extraction results for chlorophyll-a by use of undisrupted intact chlorella.
Figure 1E:
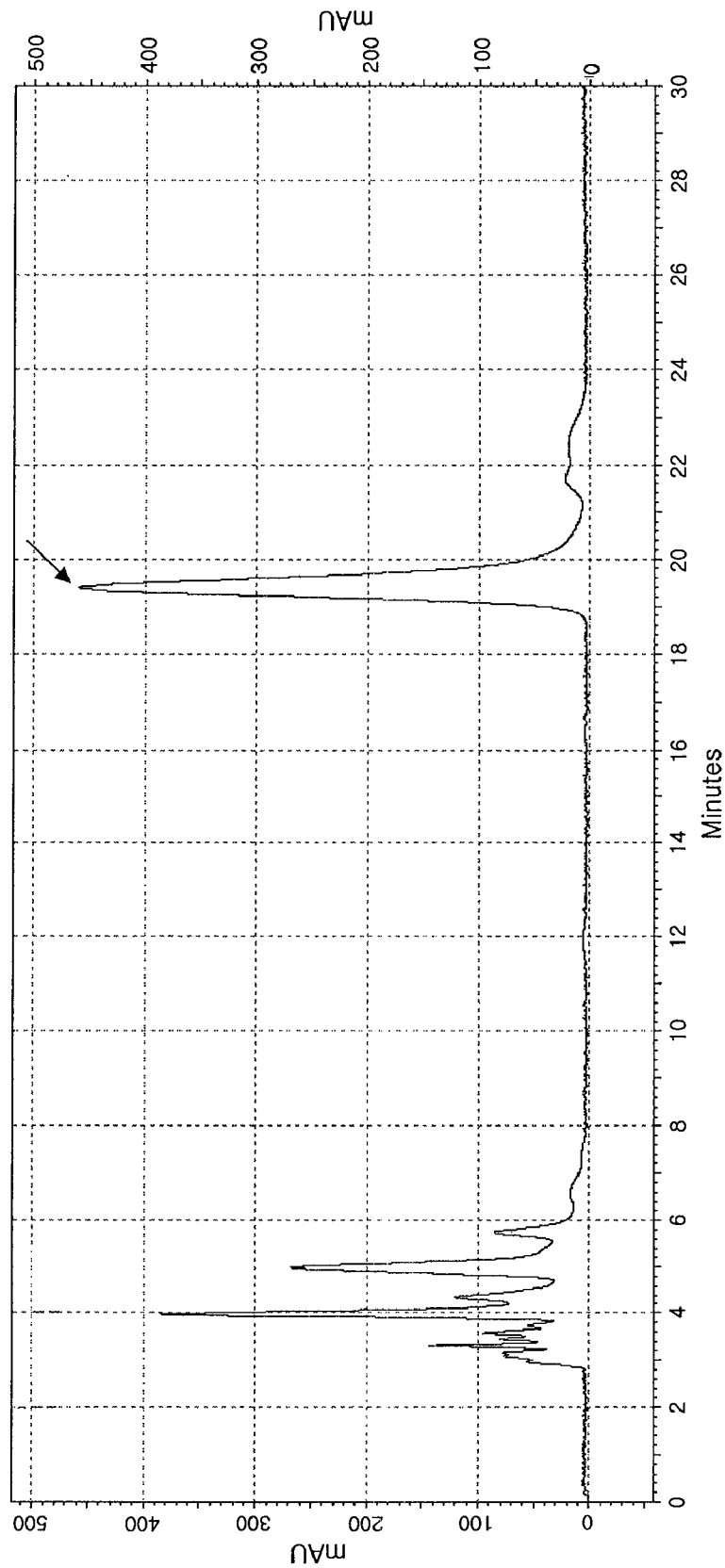
Figure 1F:
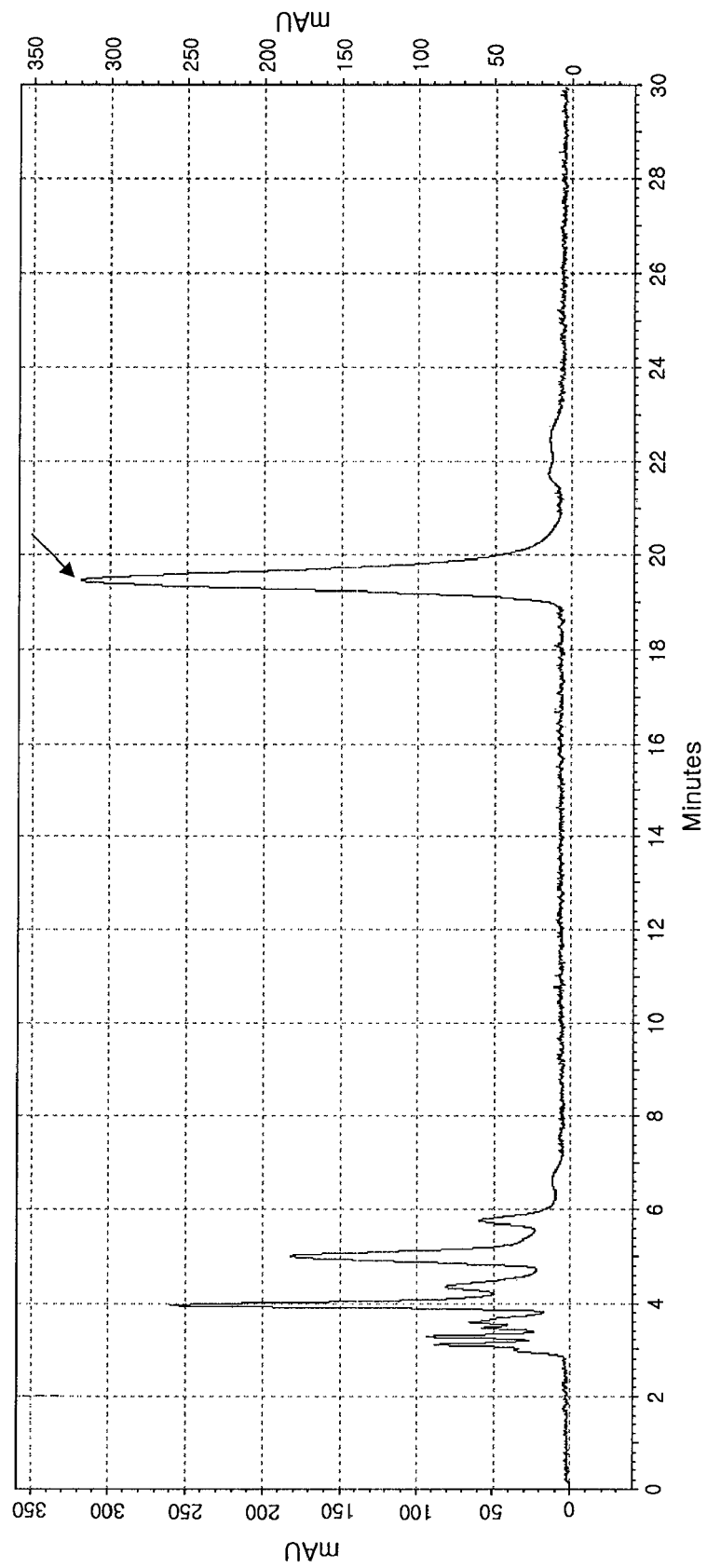

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Selection of Suitable *Chlorella*

As a starting material to obtain chlorin e6 as the final product, two samples of utrasonication disrupted *chlorella* and utrasonication undisrupted intact *chlorella* [seawater *chlorella* and *chlorella ellipsoidea*, Chlorland co, Ltd] were prepared. Next, the contents of chlorophyll-a and other ingredients of utrasonication disrupted *chlorella* and intact *chlorella* were analyzed. 100 ml of ethanol was added to 10 g respectively taken from utrasonication disrupted *chlorella* and seawater *chlorella*, followed by stirring for 30 min, 90 min, 3 hr and 12 hr, thereby obtaining extraction solutions by filtration. The extraction solutions were analyzed using HPLC (high pressure liquid chromatography), and HPLC was performed using an HPLC system (Dong-il Shimadzu Corp.) having a SPD-M10AVP column. The input volume was set as 20 μl and the flow velocity was 1 ml/min. Chlorophyll-a commercially available from Fluka was used as a reference. In FIGS. 1a-1f, the pick of chlorophyll-a was observed at about a retention time of 19.5 min.

As shown in FIGS. 1a-1f, where using intact *chlorella*, chlorophyll-a may be obtained more about 20-fold than where using ultrasonication disrupted *chlorella*. Thus, it was found that intact *chlorella* can be used to obtain a much more abundant amount of chlorin e6 than using ultrasonication disrupted *chlorella*, due to having higher yield of chlorophyll-a. Interestingly, it was found that ethanol extraction using *chlorella* itself exhibits more excellent extraction yield of chlorophyll-a than ethanol extraction by use of ultrasonication disrupted *chlorella*. In light of these, the method of this invention is very important, because it has plausible advantages: excellent extraction efficiency of chlorophyll-a and avoidance of chlorophyll-a oxidation induced in ultrasonication disruption procedure.

Example 2

Preparation Chlorin e6 from Chlorophyll-a

Protocol A
A-1: Elimination of Other Ingredients Except Chlorophyll-a from *Chlorella*

First, to remove salt in seawater *Chlorella* (*Chlorella ellipsoidea*) purchased from Chlorland co, Ltd, *Chlorella* was washed with distilled water and then precipitated by centrifuging at 5000 rpm. The precipitate was resuspended in distilled water and recentrifuged. After washing five times with distilled water and then by taking a small amount, the contents of chlorophyll-a and other ingredients were analyzed using HPLC (high pressure liquid chromatography). HPLC was performed using an HPLC system (Dong-il Shimadzu Corp.) having a SPD-M10AVP column, and a setting of up to 20 μl input volume, 1 ml/min flow velocity. Chlorophyll-a commercially available from Fluka was used as a reference. HPLC results were shown in FIG. 2a.

Figure 2A:
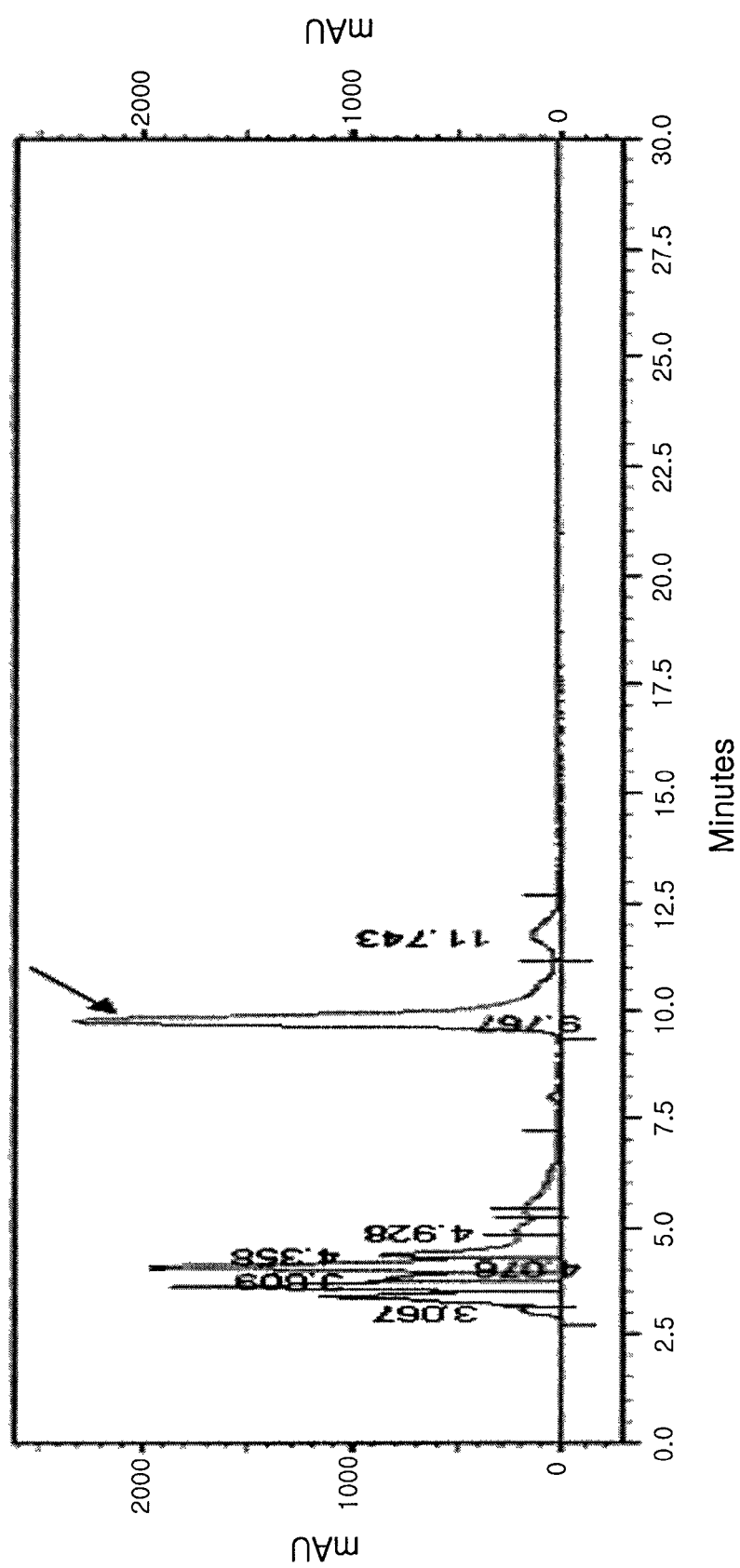
FIG. 2a is the HPLC chromatogram analyzing ingredients contained in undisrupted intact chlorella. The arrow presents the pick of chlorophyll-a.
Figure 2B:
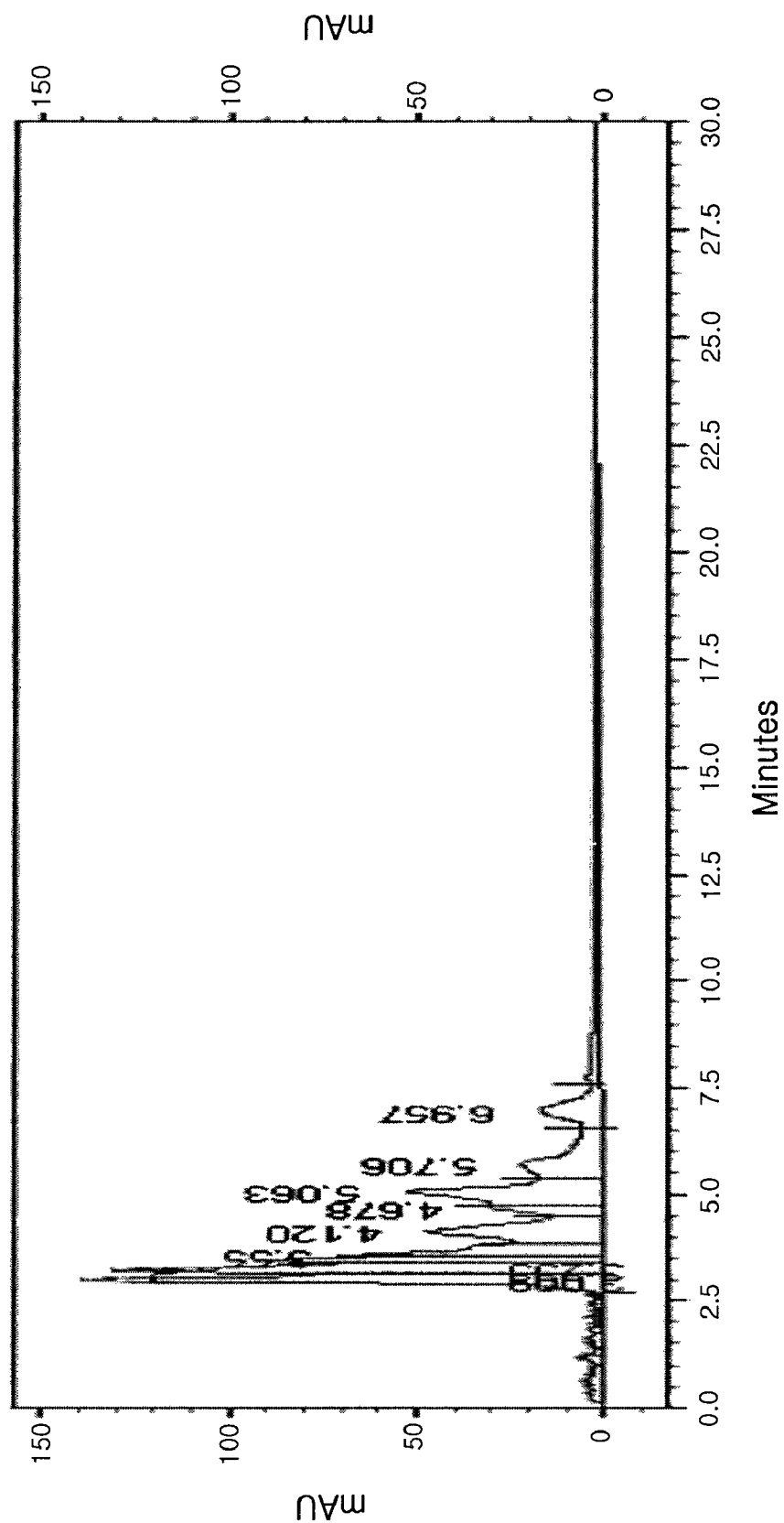
FIGS. 2b-2g represent the HPLC analysis result removing other ingredients except chlorophyll-a by washing chlorella with 60% ethanol.
Figure 2C:
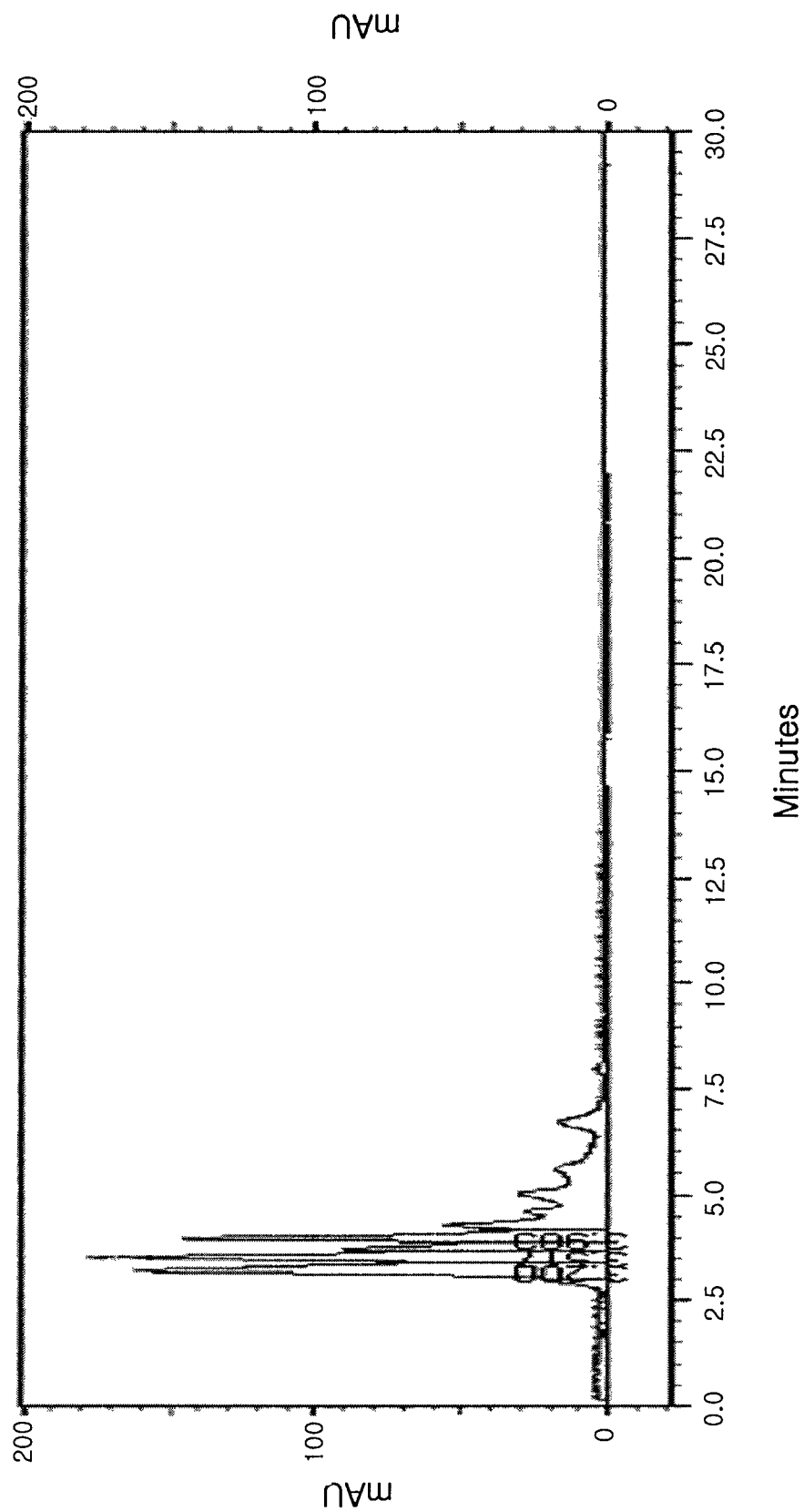
Figure 2D:
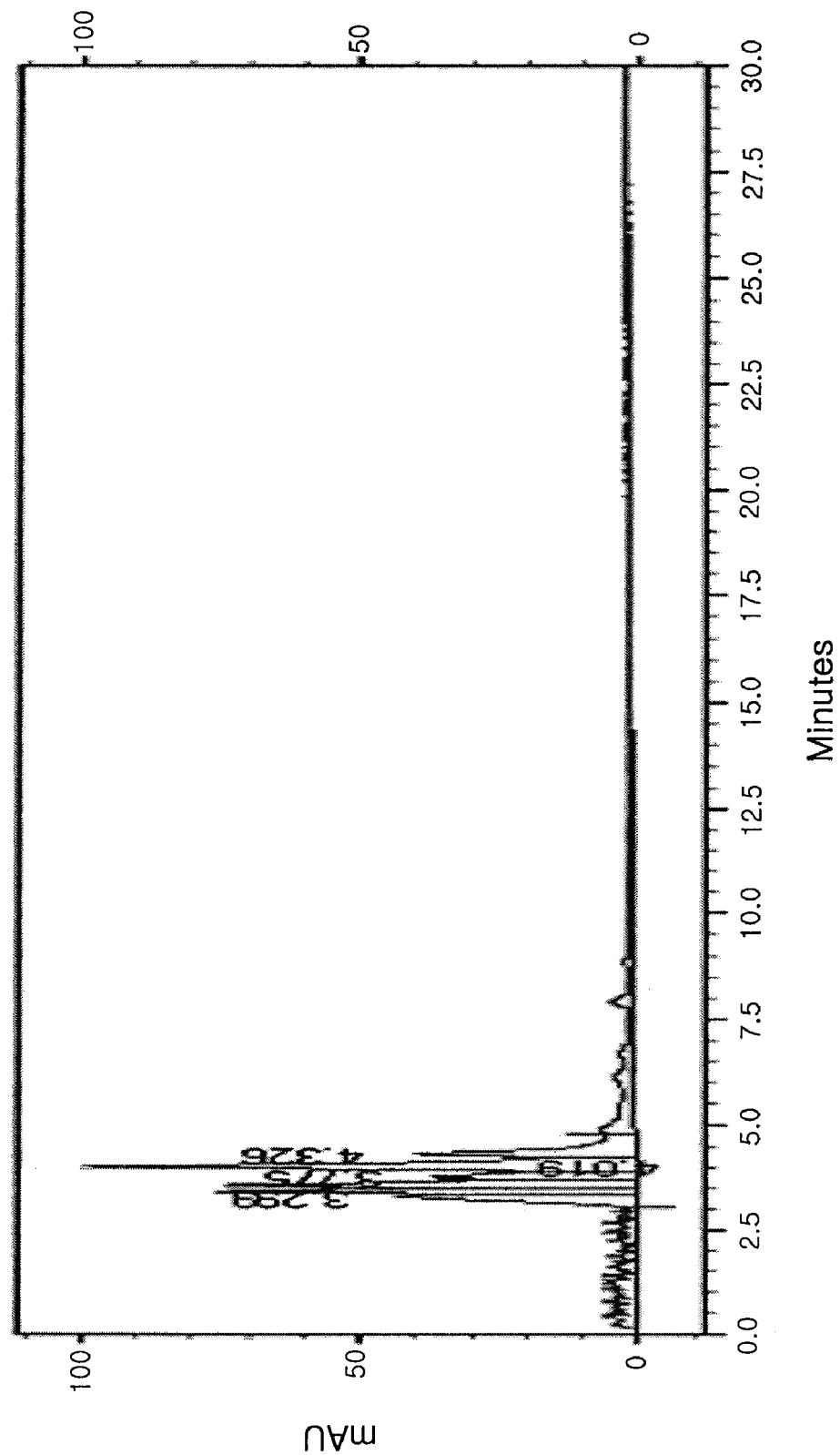
Figure 2E:
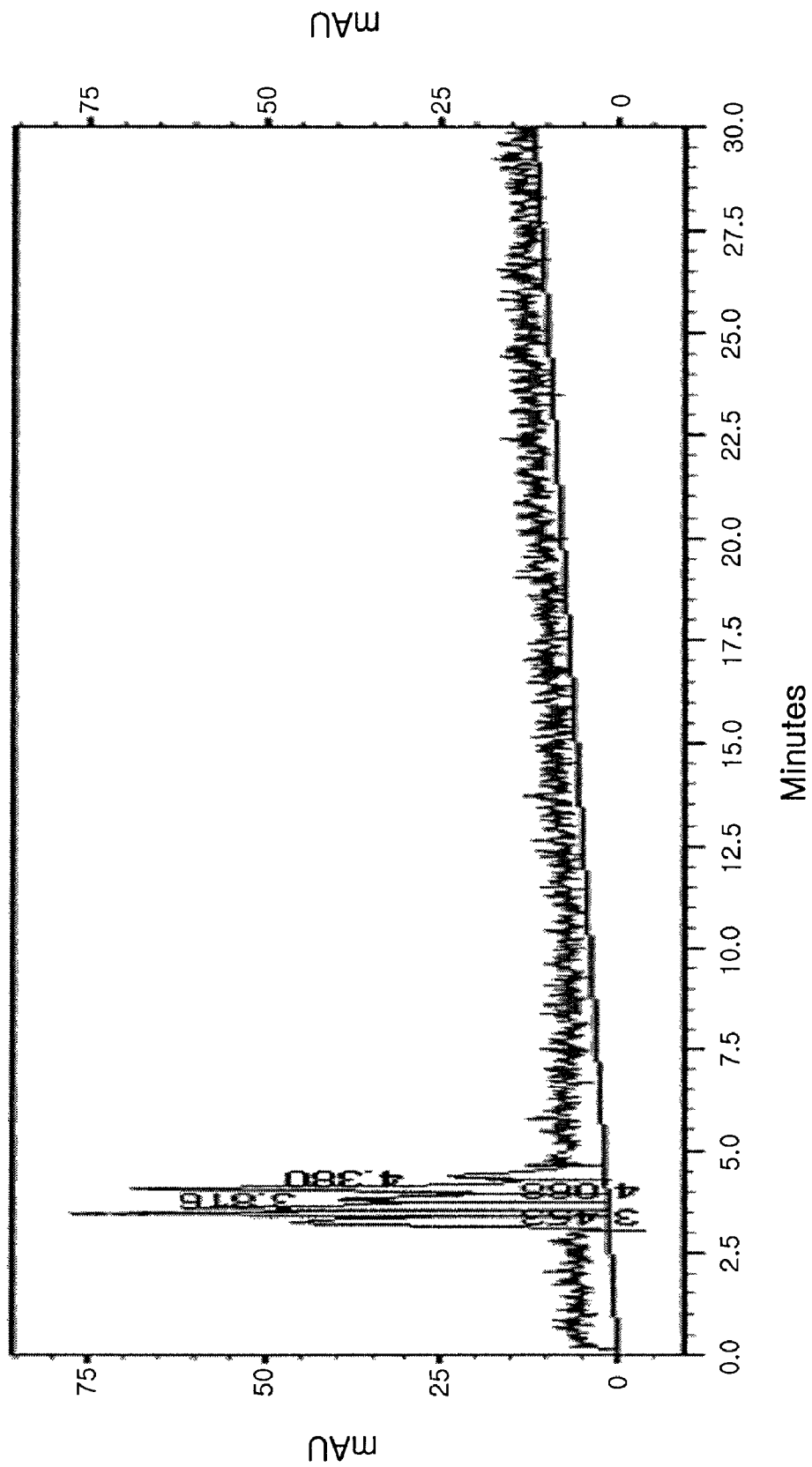
Figure 2F:
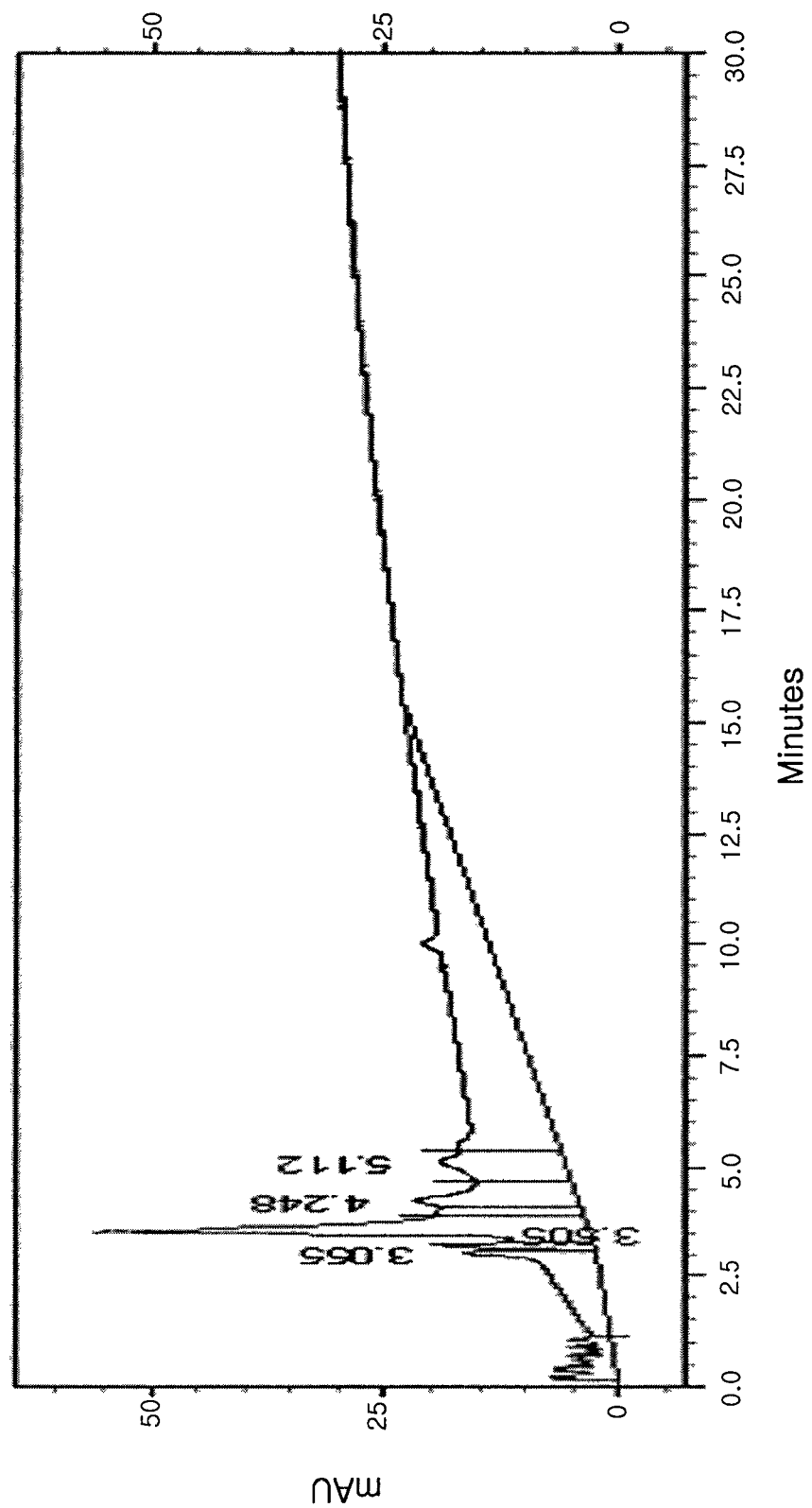
Figure 2G:
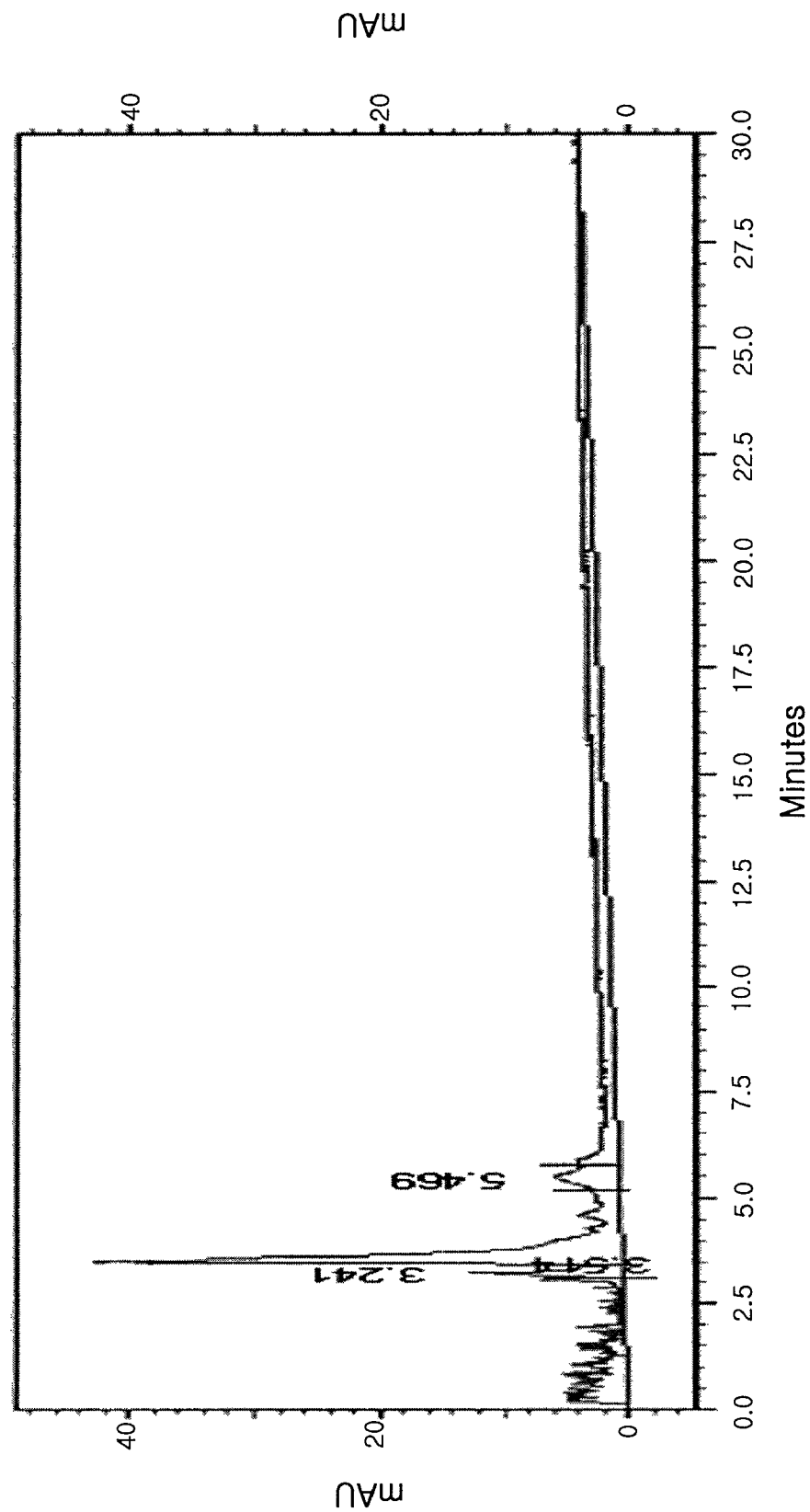

As shown in FIG. 2a, the pick of chlorophyll-a was observed at about a retention time of 9.7 min and picks of other ingredients at retention times of 2.5-7.5 min.

100 g *chlorella* removed of seawater (intact *chlorella* cells not lysed) were washed with 300 ml of 60% ethanol and then precipitated by centrifugation at 5000 rpm, thereby eliminating other ingredients at retention times of 2.5-7.5 min. These washing procedures using ethanol were conducted a total of six times. FIG. 2b-2g are the HPLC results for the supernatant produced by centrifuging in ethanol washing. As shown in FIG. 2b-2g, it was found that other ingredients shown at 2.5-7.5 min retention time were abundantly removed by washing procedures using 60% ethanol.

Meanwhile, where the washing procedure was performed using ethanol of more than 80% concentrations, chlorophyll-a was extracted and other ingredients could not be eliminated. In addition, where the washing procedure was carried out using ethanol solutions of 20%, 40% and 50% concentrations, the removal of other ingredients became poor compared with 60% ethanol.

Thus, these results demonstrated that 60% ethanol is the most preferable washing solution. Namely, 60% ethanol as washing solutions effectively extracts other ingredients from *chlorella* cells except chlorophyll-a, leading to relatively higher content of chlorophyll-a in *chlorella* cells washed.

A-2: Extraction I of Chlorophyll-a from *Chlorella* Removed of Other Ingredients Following the addition of 1 L of 100% ethanol to the 100 g *chlorella* eliminated of other ingredients, chlorophyll-a was extracted by stirring for 3 hr. *Chlorella* cells used for extraction procedure were not lysed by sonication and their undisrupted form itself was used. Although chlorophyll-a is generally extracted by treating cell lysates with organic solvents, the present example uses *chlorella* cells per se rather than their lysates. The extraction results were shown in FIG. 2h.

Figure 2H:
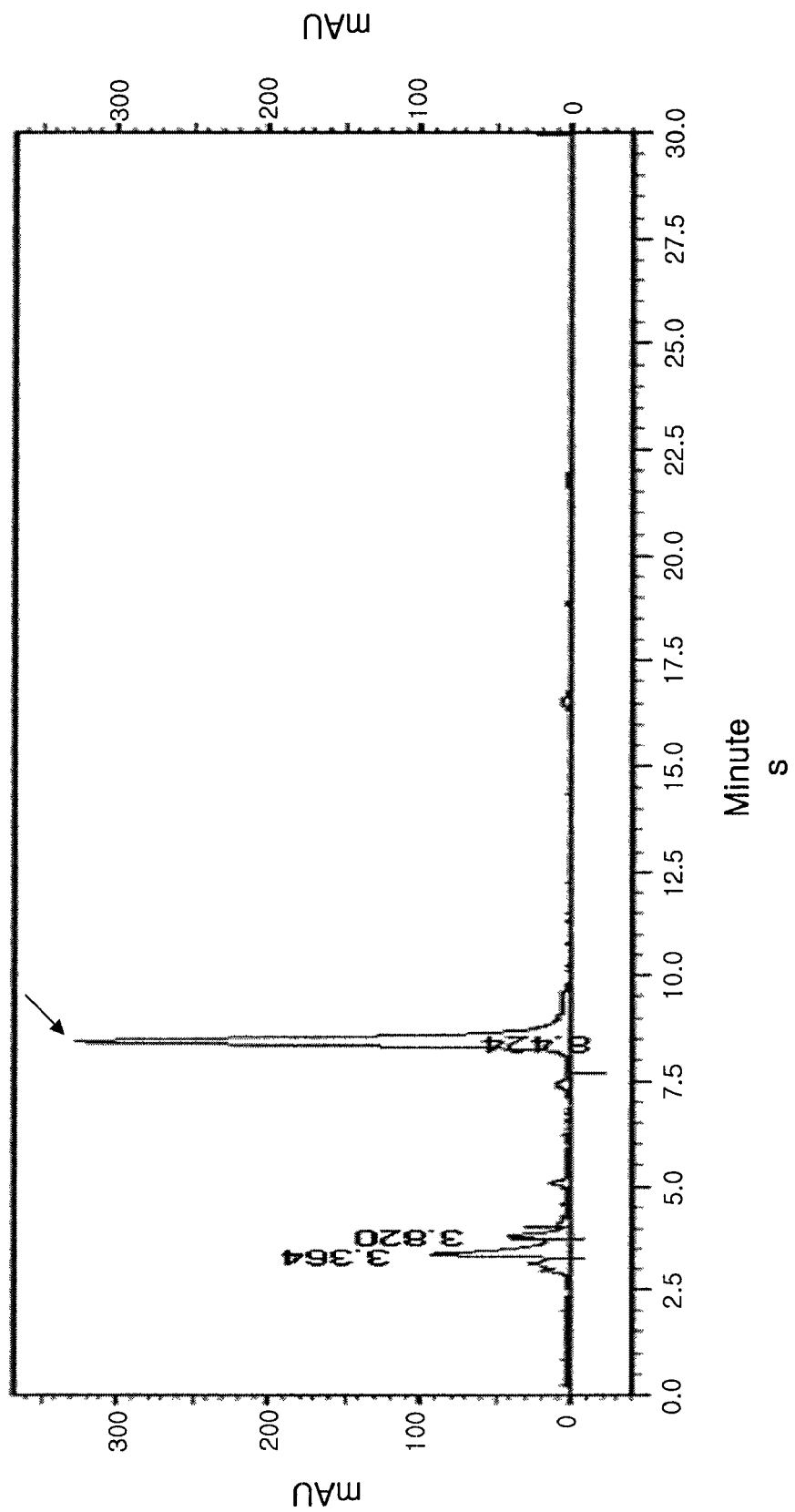
FIG. 2h shows the HPLC analysis result extracting chlorophyll-a with 100% ethanol. The arrow presents the pick of chlorophyll-a.

As represented in FIG. 2h, the pick of chlorophyll-a was observed at about a retention time of 8.4 min and other ingredients of a retention times of 2.5-7.5 min observed in FIG. 2a abundantly removed. Furthermore, it was found that contents of chlorophyll-a (i.e., purity) are 76.92% in chromatogram of HPLC. Meanwhile, the yield for chlorophyll-a of protocol A was 7.89%.

Protocol B

First, to remove salt in seawater *Chlorella* purchased from Chlorland co, Ltd, *Chlorella* was washed with distilled water and then precipitated by centrifuging at 5000 rpm. The precipitate was resuspended in distilled water and recentrifuged. After washing five times with distilled water and then by taking a small amount, the contents of chlorophyll-a and other ingredients were analyzed by HPLC (high pressure liquid chromatography). HPLC was performed using an HPLC system (Dong-il Shimadzu Corp.) having a SPD-M10AVP column, and a setting of up to 20 μl input volume, 1 ml/min flow velocity. Chlorophyll-a commercially available from Fluka was used as a reference. 100 g *chlorella* removed of seawater (intact *chlorella* cells not lysed) were washed with 500 ml of 100% ethanol and then precipitated by centrifugation at 5000 rpm, followed by filtration of only supernatant chlorophyll extraction solution. 70 ml of dioxane and 70 ml of distilled water were added to the chlorophyll extract, and kept in cold storage for over 5 hr at −20° C. to induce precipitation. Then, the precipitates were filtered and washed up with water, thereby obtaining chlorophyll-a. Afterwards, for preparing chlorin e6, the precipitates were dissolved in 100% of ethanol.

Figure 2I:
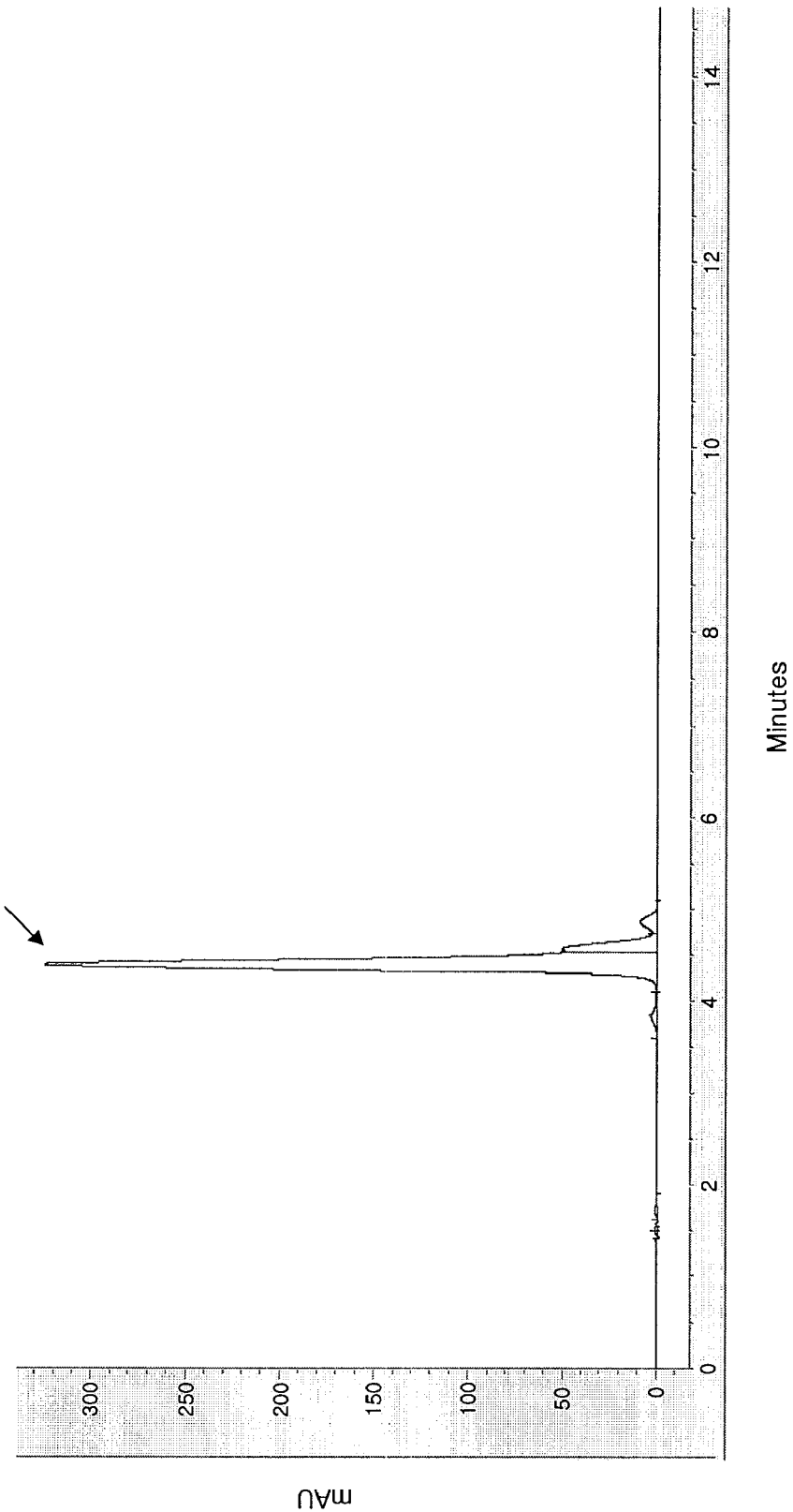
FIG. 2i shows the HPLC chromatogram for chlorophyll-a prepared according to the method for preparing chlorophyll-a by use of dioxane. The arrow presents the pick of chlorophyll-a.

As shown in FIG. 2i, the main pick of chlorophyll-a was observed at about a retention time of 4.3 min and other picks were seldom observed. Furthermore, it was found that contents of chlorophyll-a (i.e., purity) are 84.93% in chromatogram of HPLC. Meanwhile, the yield for chlorophyll-a of protocol B was 4.26%.

The experimental results demonstrate that chlorophyll-a may be obtained with high yield through simple processes using dioxane.

Example 3

Preparation Chlorin e6 from Chlorophyll-a

Example 3-1

Production of Pheophytin a

Figure 3A:
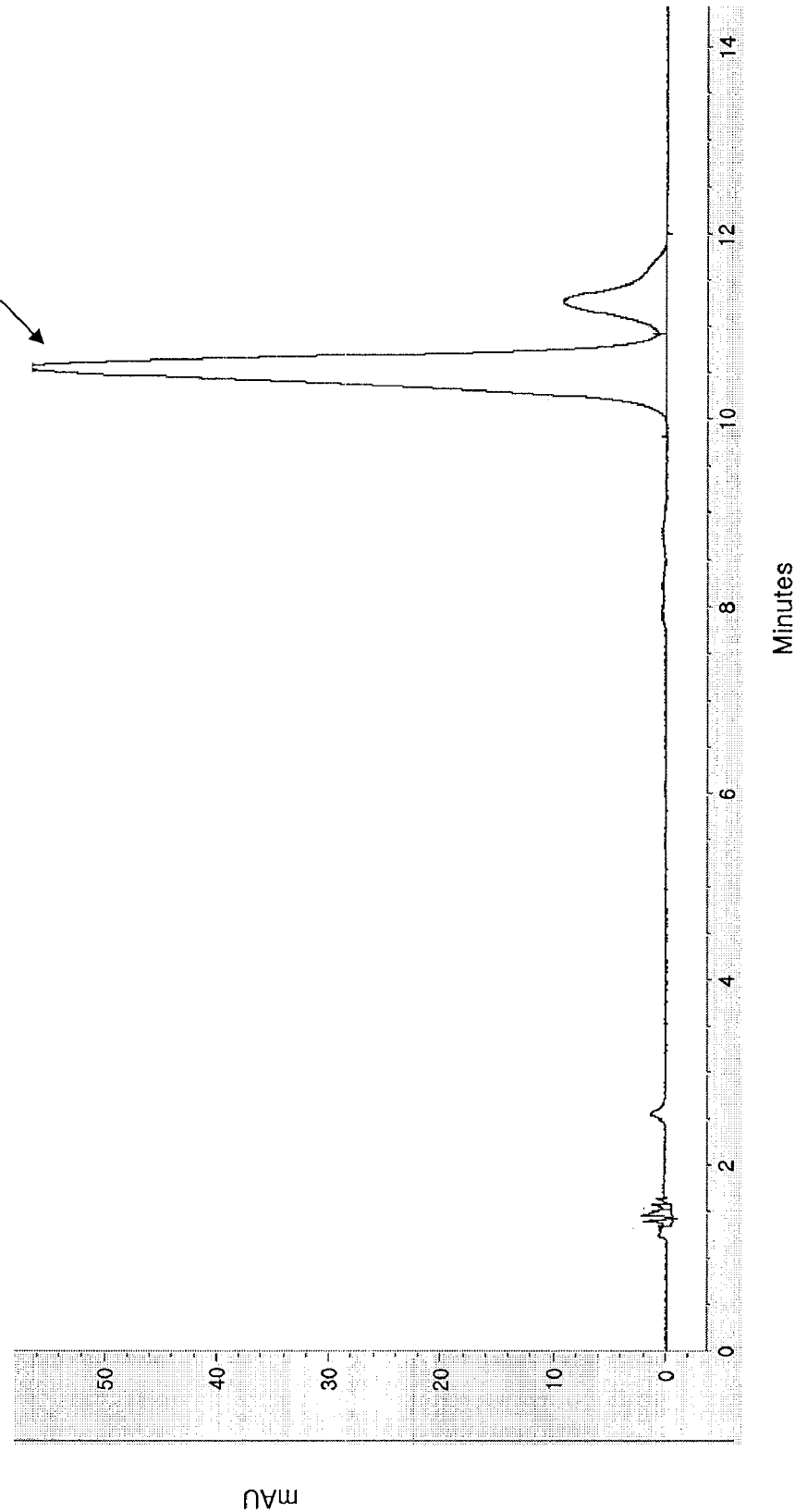

The extracts were adjusted to pH 2-3 by adding 5-10 ml of 1 N HCl per 1 L of the ethanol extract comprising chlorophyll-a obtained in protocol A of Example 2, and then $Mg^{2+}$ was eliminated from chlorophyll-a by stirring for 3 hr, thereby obtaining pheophytin a (FIG. 3a). Then, the pheophytin a solution with black color was precipitated by keeping in cold storage for 3-6 hr at −23° C., followed by filtration.

Example 3-2

Production of chlorin e6

Protocol A

Figure 3B:
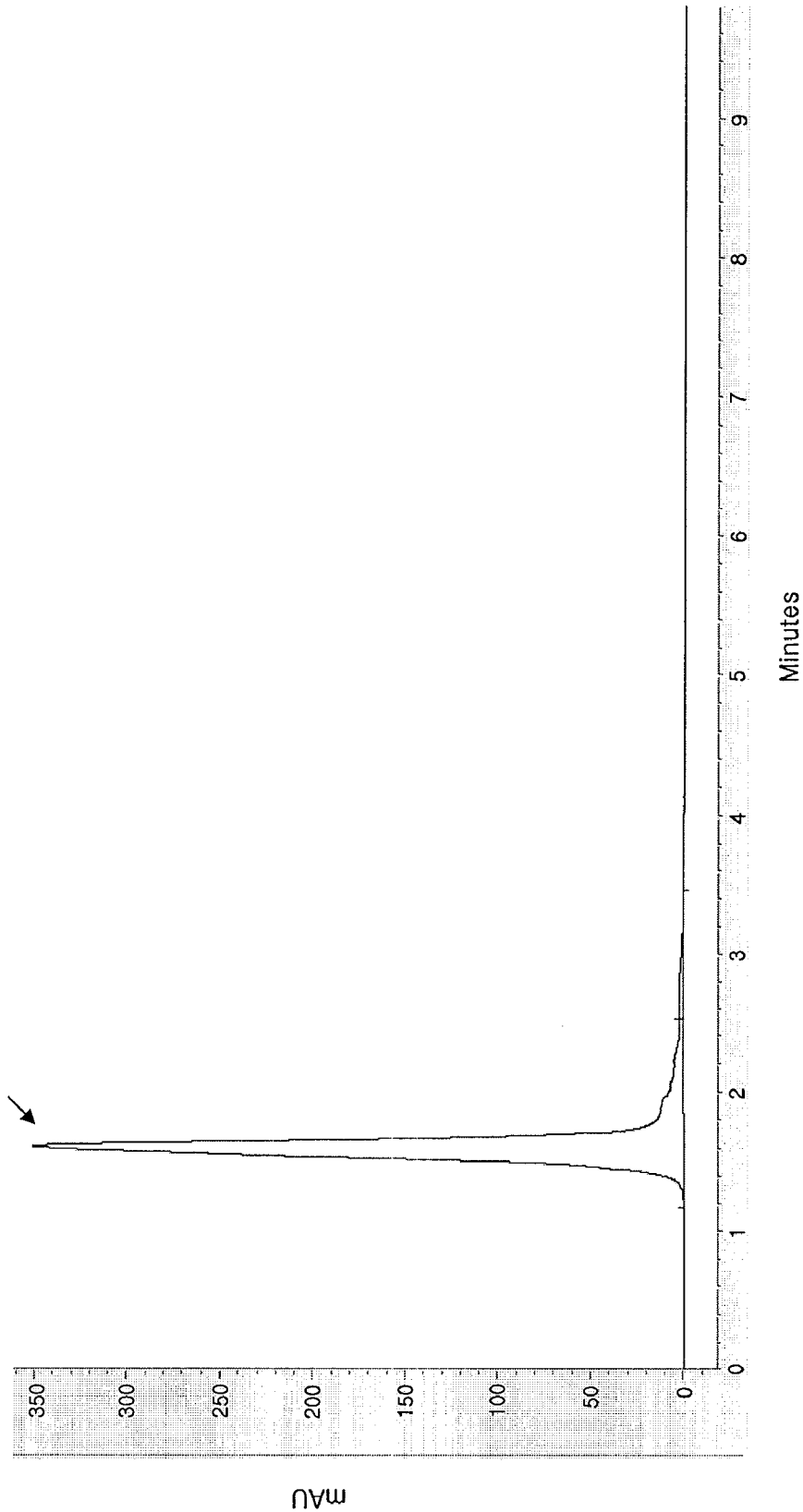
FIG. 3b shows the HPLC chromatogram for chlorin e6 prepared according to protocol A of the present method. The arrow presents the pick of chlorin e6.

After dissolving the pheophytin a precipitates of Example 3-1 with acetone, acetone was eliminated by evaporation. The pheophytin a was dissolved in 1 L of 100% ethanol, and a filtered solution comprising pheophytin a solution was adjusted to pH 13-14 by adding 5-10 ml of 1 N NaOH, thereby producing chlorin e6 from pheophytin a by stirring for 12 hr. Afterward, the produced chlorin e6 was neutralized by adding 1 N HCl to the resultants, and then filtered, followed by eliminating completely ethanol (FIG. 3b). As represented in the graph of FIG. 3b, the pick of chlorin e6 was observed at about a retention time of 4.987 min and it was found that contents of chlorin e6 (purity) are 97.66%.

Finally 48.6 g of chlorin e6 was given from 100 g of *chlorella* (yield: 4.86%).

In addition, to prepare the salt form of chlorin e6, 3 equivalents of $NaHCO_3$ or $NH_4HCO_3$ were dissolved in ice water, added to chlorin e6, and then water was filtered out to yield the salt form of chlorin e6 by freeze-drying.

Protocol B

Figure 3C:
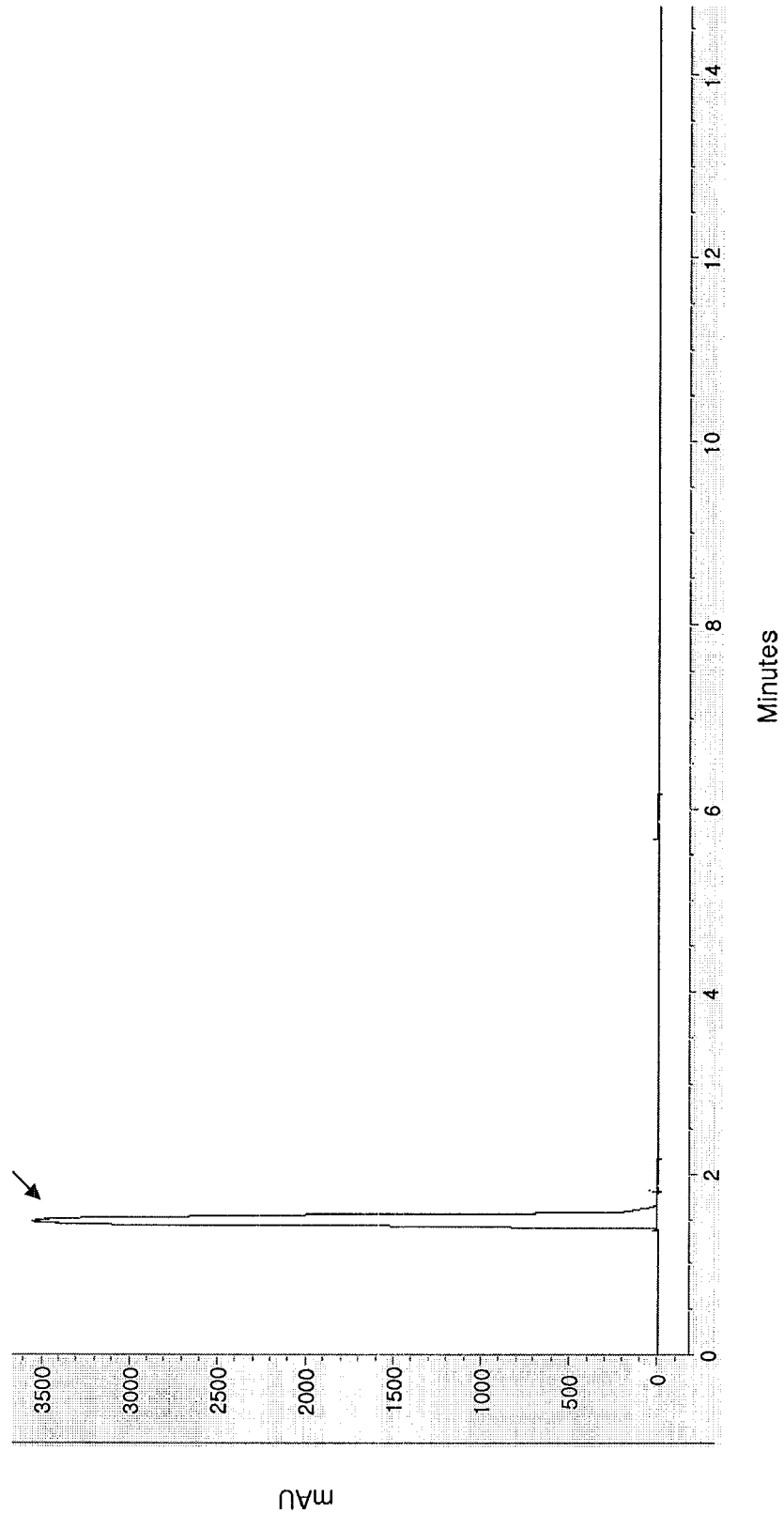
FIG. 3c shows the HPLC chromatogram for chlorin e6 prepared according to protocol B of the present method. The arrow presents the pick of chlorin e6.

Pheophytin a precipitates of Example 3-1 were dissolved in 1 L of acetone, adjusted to pH 13-14 by adding 5-10 ml of 1 N NaOH, and then stirred for 12 hr to produce chlorin e6 from pheophytin a. To produce chlorine e6 Na salt, the filtered precipitates were washed with acetone and nucleic acid in order, and then dissolved in a small amount of water. After the filtration of chlorin e6 solution by a soluble membrane filter, the final chlorin e6 Na salt was obtained by freeze-drying (FIG. 3c). The final chlorin e6 Na salt showed a powder form. In the treatment of 10 L of *chlorella* (1-1.5 kg after centrifugation), the yield of the final Na salt chlorin e6 was 2.5-3.0% as 25-30 g. In addition, the purity for chlorin e6 was 99.83%.

According to protocol B, chlorin e6 Na salt was directly formed by NaOH treatment in the production procedure of chlorin e6. It was found that this fact has a great difference from protocol A.

This invention extracts chlorophyll-a by use of undisrupted *chlorella* cells themselves, thereby preparing chlorin e6 from the chlorophyll-a extract. The high contents of chlorophyll-a may be obtained by the pretreatment procedure of *chlorella* cells themselves selected in this invention. The present method is performed according to relatively simple procedures, and is suitable in the mass production of chlorin e6.

Having described a preferred embodiment of the present invention, it is to be understood that variants and modifications thereof falling within the spirit of the invention may become apparent to those skilled in this art, and the scope of this invention is to be determined by the appended claims and their equivalents.

What is claimed is:

1. A method of preparing a chlorophyll-a extract comprising the steps of:
   (a) treating an undisrupted seawater *chlorella* with 50-65% ethanol to extract non-chlorophyll-a ingredients,
   (b) precipitating the ethanol-treated *chlorella* to separate the ethanol-treated *chlorella* from the extracted non-chlorophyll-a ingredients,
   (c) treating the precipitated *chlorella* with 98-100% ethanol to extract chlorophyll-a, and
   (d) removing the 98-100% ethanol-treated *chlorella*, thereby obtaining the chlorophyll-a extract.

2. The method according to claim 1, wherein the concentration of ethanol in step (a) is 58-62%.

3. The method according to claim 1, wherein the steps (a) and (b) are repeatedly performed 3-6 times.

4. The method according to claim 1, wherein the yield of chlorophyll-a extracted from *chlorella* is 7-9 dry weight %, and the purity of chlorophyll-a is 72-80%.

* * * * *